United States Patent
Huber et al.

(10) Patent No.: US 8,975,602 B2
(45) Date of Patent: Mar. 10, 2015

(54) ACTIVE FLOOR FOR PROTON THERAPY

(71) Applicant: ProNova Solutions, LLC, Knoxville, TN (US)

(72) Inventors: Jonathan Huber, Knoxville, TN (US); Joseph C. Matteo, Walland, TN (US); Tyler Evors, Knoxville, TN (US); Aaron Jacques, Knoxville, TN (US)

(73) Assignee: ProNova Solutions, LLC, Knoxville, TN (US)

( * ) Notice: Subject to any disclaimer, the term of this patent is extended or adjusted under 35 U.S.C. 154(b) by 0 days.

(21) Appl. No.: 14/064,711

(22) Filed: Oct. 28, 2013

(65) Prior Publication Data

US 2014/0121441 A1 May 1, 2014

Related U.S. Application Data

(60) Provisional application No. 61/719,129, filed on Oct. 26, 2012, provisional application No. 61/880,535, filed on Sep. 20, 2013.

(51) Int. Cl.
  *G21K 5/04* (2006.01)
  *A61N 5/10* (2006.01)
  *A61B 6/04* (2006.01)

(52) U.S. Cl.
  CPC ............ *A61N 5/1081* (2013.01); *A61B 6/0407* (2013.01); *A61N 2005/1087* (2013.01)
  USPC ................. 250/492.3; 250/492.1; 250/396 R; 600/1

(58) Field of Classification Search
  CPC ..... A61N 5/01; A61N 5/1007; A61N 5/1048; A61N 5/1065; A61N 5/1077; A61N 5/1081
  USPC ............ 250/396 R, 397, 492.1, 492.2, 492.3; 600/1
  See application file for complete search history.

(56) References Cited

U.S. PATENT DOCUMENTS

| | | | |
|---|---|---|---|
| 6,094,760 A | 8/2000 | Nonaka | |
| 8,223,920 B2 | 7/2012 | Amelia et al. | |
| 2004/0111134 A1* | 6/2004 | Muramatsu et al. | 607/88 |
| 2007/0217575 A1 | 9/2007 | Kaiser et al. | |
| 2008/0029706 A1 | 2/2008 | Kaiser et al. | |
| 2008/0189859 A1* | 8/2008 | Sloan et al. | 5/601 |
| 2008/0219407 A1* | 9/2008 | Kaiser et al. | 378/65 |
| 2011/0299657 A1* | 12/2011 | Havelange et al. | 378/65 |

OTHER PUBLICATIONS

PCT, International Searching Authority; Int'l Search Report; Form PCT/ISA/220; Date of Mailing: Mar. 27, 2014.

* cited by examiner

*Primary Examiner* — Nicole Ippolito
(74) *Attorney, Agent, or Firm* — Pitts & Lake, P.C.

(57) ABSTRACT

An operator positioning apparatus for a proton treatment system includes: a proton beam nozzle to emit a proton beam to a targeted region of a patient; a gantry wheel having a front face to support the proton beam nozzle to direct the proton beam to an isocenter of the gantry wheel corresponding to a center of the targeted region, wherein the gantry wheel rotates the proton beam nozzle around the isocenter; an active floor that horizontally translates across the front face of the gantry wheel, the active floor having an opening having a width through which the proton beam nozzle protrudes when the proton beam nozzle is located below the targeted region.

20 Claims, 17 Drawing Sheets

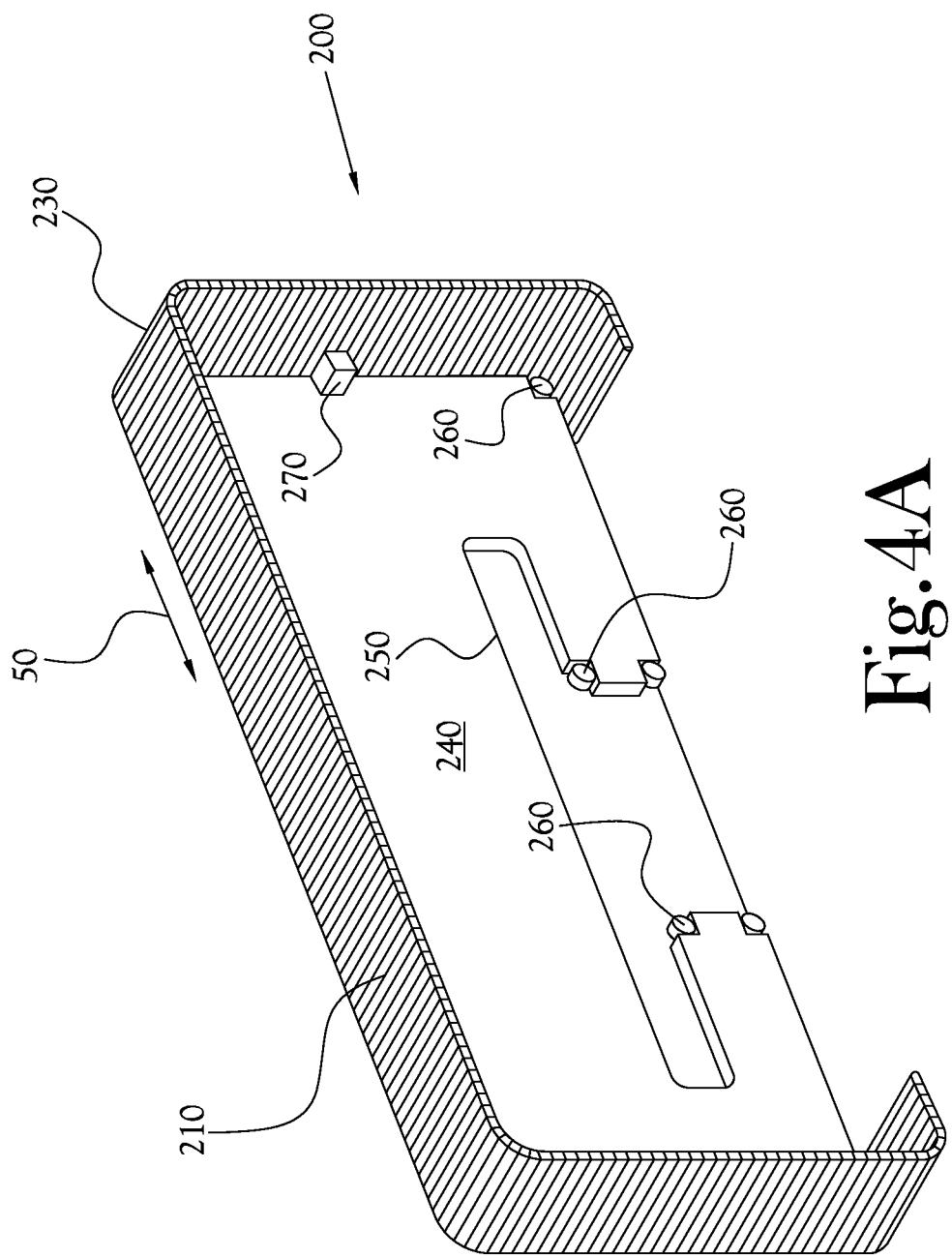

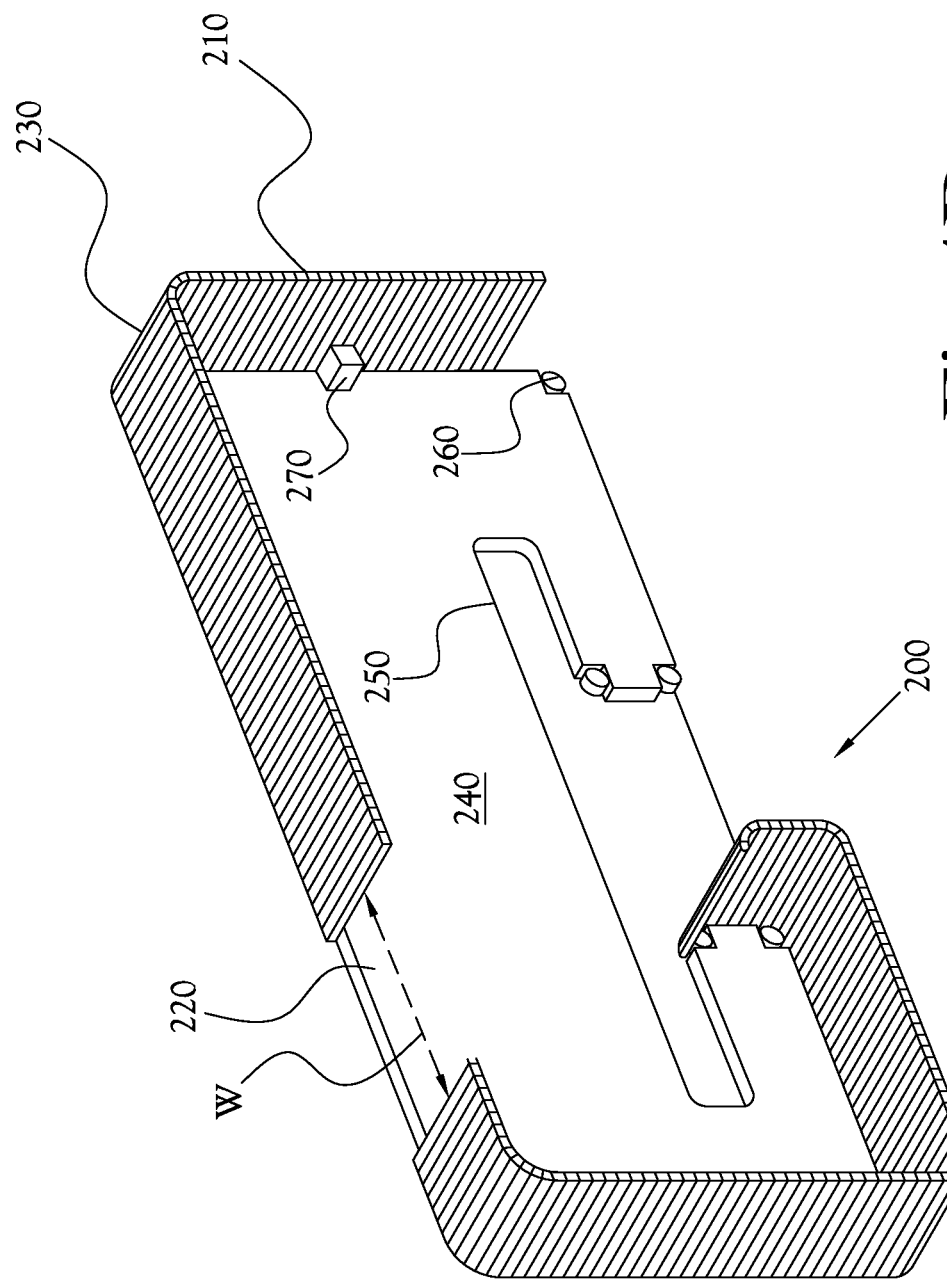

ically takes about 6 months to install the system (including gantry) on site and an additional 12 months to commission the equipment. This lengthy build time is largely associated with the fine adjustment of the magnetic fields required to direct protons through the gantry and the related beam accuracy demands. Due to the large size and extensive construction of the PT system, it is necessary to provide a technician or operator access to equipment from the patient treatment side of the PT system gantry wheel.
ACTIVE FLOOR FOR PROTON THERAPY

CROSS-REFERENCE TO RELATED APPLICATIONS

This application claims the benefit of provisional application Ser. No. 61/719,129 filed Oct. 26, 2012 and provisional application Ser. No. 61/880,535 filed Sep. 20, 2013, the entirety of which are hereby incorporated herein by reference.

FIELD OF INVENTION

The present application relates to proton therapy for cancer treatment, and more particularly, to an active floor to accommodate a rotating gantry system that aligns a proton delivery mechanism.

BACKGROUND

Proton Therapy (PT) is a cancer treatment technology that uses high energy protons to penetrate a patient's body and deposit energy into treatment areas such as cancerous tumors. PT systems commonly implement a rotating gantry wheel that directs the proton beam to the patient from any angle between zero and 360 degrees. This allows the physician to design a treatment plan that attacks cancerous tumors from different angles and reduces radiation damage to critical organs and/or healthy tissue.

One of the challenges facing PT systems is to maintain proper alignment between the proton delivery nozzle and a patient. It is known to provide a cantilevered patient bed that facilitates positioning of the patient treatment area at the isocenter of the rotating gantry wheel.

Another challenge facing PT systems is the time it takes to construct and implement a working system. For example, it typically takes about 6 months to install the system (including gantry) on site and an additional 12 months to commission the equipment. This lengthy build time is largely associated with the fine adjustment of the magnetic fields required to direct protons through the gantry and the related beam accuracy demands. Due to the large size and extensive construction of the PT system, it is necessary to provide a technician or operator access to equipment from the patient treatment side of the PT system gantry wheel.

Efforts regarding such systems have led to continuing developments to improve their versatility, practicality and efficiency.

BRIEF DESCRIPTION OF THE FIGURES

The following example embodiments are representative of example techniques and structures designed to carry out the objects of the present general inventive concept, but the present general inventive concept is not limited to these example embodiments. In the accompanying drawings and illustrations, the sizes and relative sizes, shapes, and qualities of lines, entities, and regions may be exaggerated for clarity. A wide variety of additional embodiments will be more readily understood and appreciated through the following detailed description of the example embodiments, with reference to the accompanying drawings in which:

FIGS. 4a-4d are cutaway isometric diagrams of an example embodiment active floor system, with a floor opening located in different positions;

DETAILED DESCRIPTION

Reference will now be made to the example embodiments of the present general inventive concept, examples of which are illustrated in the accompanying drawings and illustrations. The example embodiments are described herein in order to explain the present general inventive concept by referring to the figures.

Figure 1:
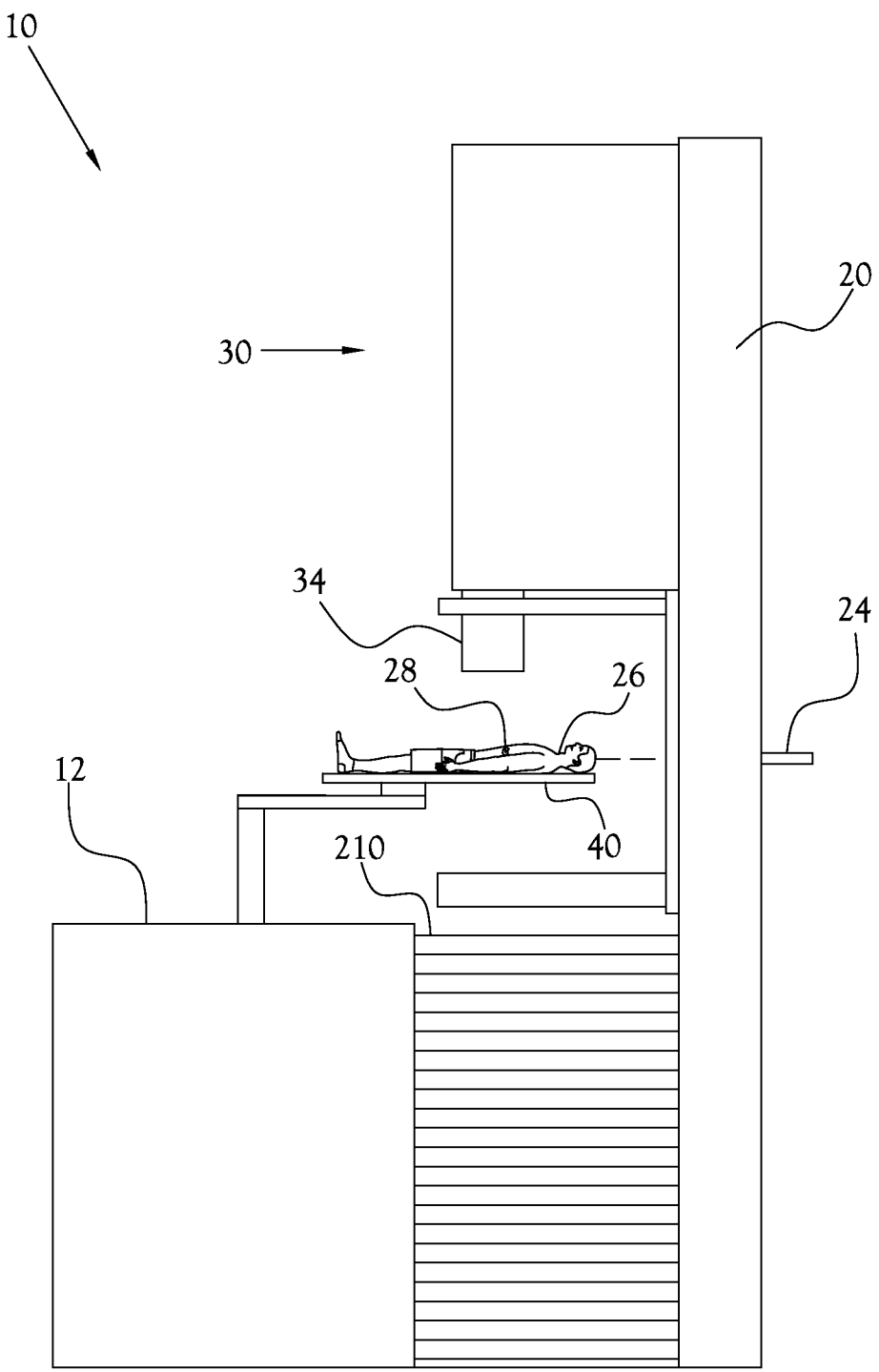
FIG. 1 is a graphic schematic side view diagram of an example embodiment of a proton therapy system.

FIG. 1 illustrates an example embodiment of a proton therapy (PT) system 10 wherein a gantry wheel 20 rotates a proton beam generator nozzle 34 about an axis of rotation 24. A proton beam generator directs a proton beam through a nozzle 34 from any angle between zero and 360 degrees toward a patient 26 lying on bed 40 near the isocenter 28 of the gantry wheel which corresponds to a treatment region of a patient. The gantry system 10 may include a mezzanine platform 12 support system and active (or rolling) floor 210 for a technician or operator to walk on, enabling access to a patient, magnets, nozzles, achromat, hoses from a beamline, cooling system, etc. for service or replacement. The active floor may be supported by an active floor system 200, described herein.

Figure 2:
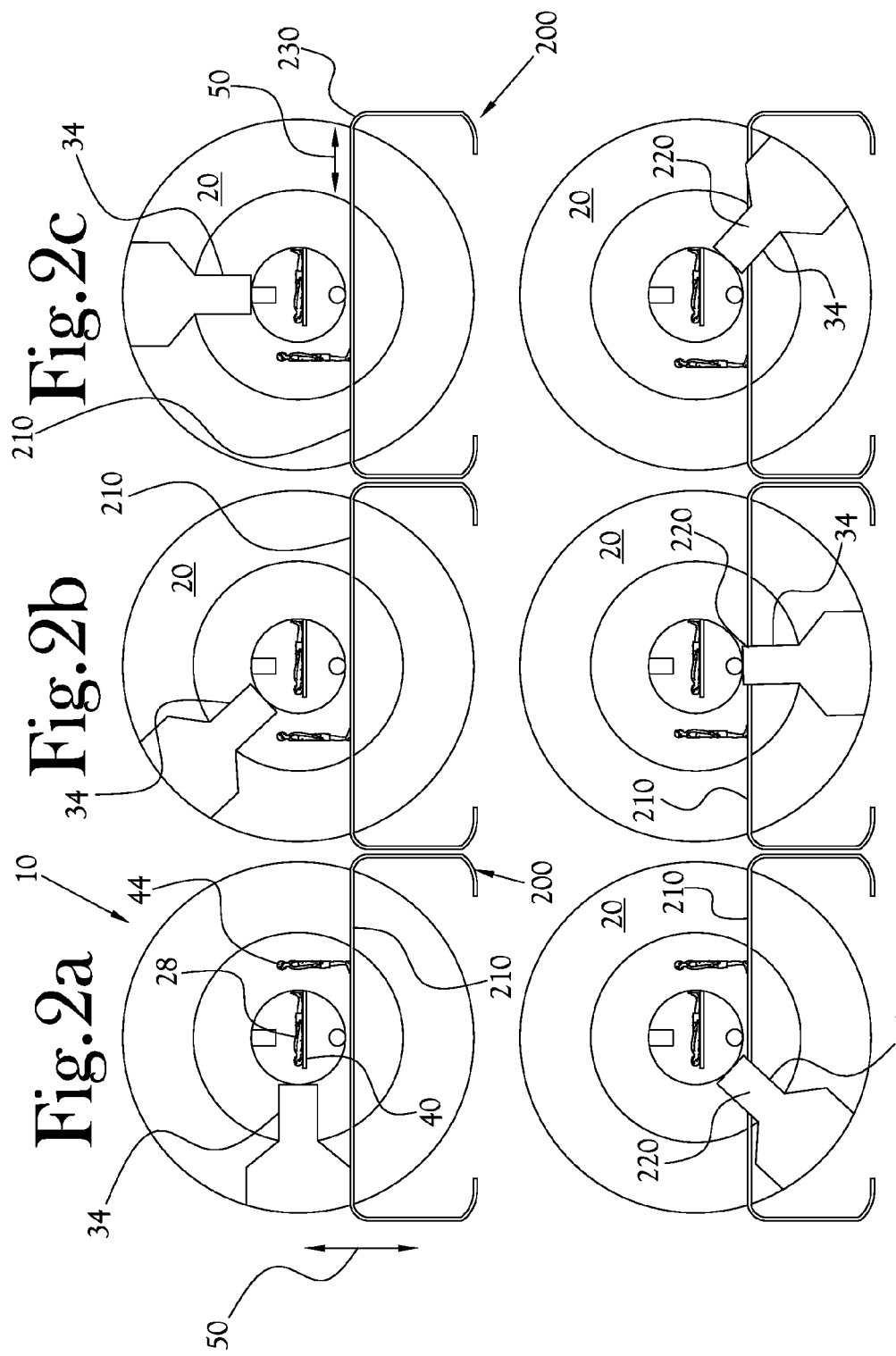
FIGS. 2a-2f are graphic schematic front view diagrams of an example embodiment proton therapy system with a proton beam generator nozzle in different positions.

FIGS. 2a-2f illustrate various views depicting an example proton beam nozzle apparatus 34 which is mounted on and rotated by a gantry 20 from a neutral or 0° angle in FIGS. 2a, to 45° in FIGS. 2b, to 90° in FIGS. 2c, to 225° in FIGS. 2d, to 270° in FIGS. 2e, to 315° in FIG. 2f. An example embodiment active floor system 200 provides an active platform 210 on which an operator 44 may stand on, the floor moving in directions indicated by arrow 50. The active floor 210 has an opening 220 provided therein for providing clearance for the proton beam nozzle apparatus 34 when the beam nozzle 34 is rotated underneath the patient, such as is shown in FIGS. 2d-2f. As the beam nozzle 34 rotates around, it moves into and out of the opening in the active floor.

Figures 3, 5:
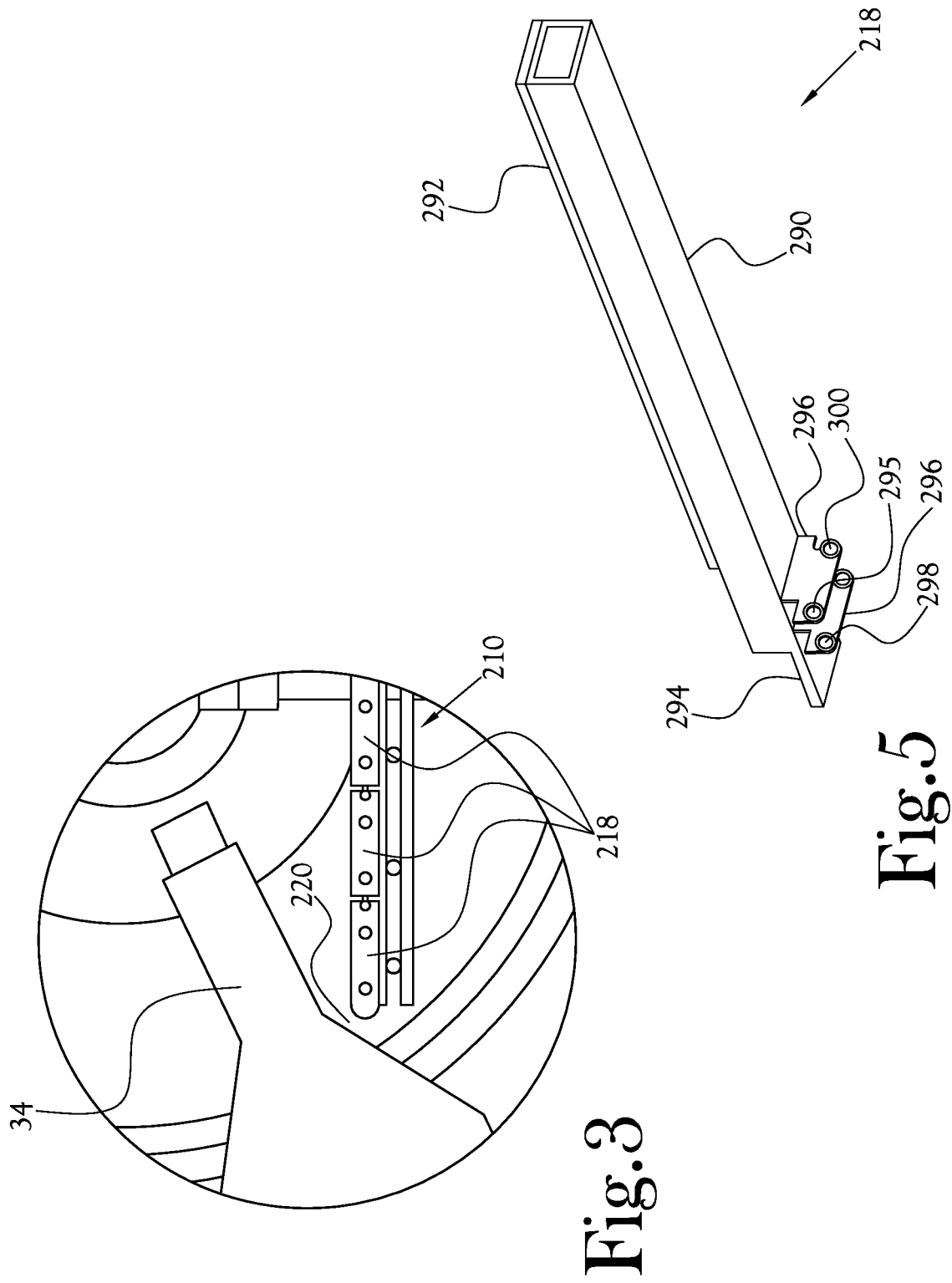
FIG. 3 is a magnified schematic front view of a portion of an example embodiment proton therapy system.
FIG. 5 is an isometric view of an example embodiment slat for an active floor system.

FIG. 3 provides an example embodiment of an active floor 210 having an opening 220 provided therein through which a proton beam nozzle 34 extends. The floor 210 may be a track comprised of a plurality of slats or links 218 that are rotatably or pivotally linked or locked together or interconnected and form a substantially rigid or solid rail which can round corners 230 but still support a person. The slats may be connected utilizing revolute joints (also called pin joints or hinge joints) in kinematic pairs. The active floor may include two sections fabricated from a plurality of interconnected slats.

FIGS. 4a-4d illustrate an example embodiment of an active floor system 200, wherein the floor moves in directions illustrated by arrow 50. The floor may be comprised of a plurality of rotatable interconnected slats. The floor moves or slides within a circuitous track disposed within a housing 240. The housing may be comprised of two opposing sides that may be mirror images of each other. For illustration only, only one side is shown in FIGS. 4a-4d. The track(s) 250 keeps the active floor captured in place and provides support so that the track does not bow or become displaced from the weight of an operator standing of the floor.

An example embodiment track may be arranged in a circuitous path in order to accommodate a longer floor than a rectangular path track would. In an example embodiment, the track may be routed or arranged linearly at the top and sides of the floor assembly and in a shape similar to a block T at the bottom of the assembly, wherein the T track extends into the interior of the floor box assembly 200. In an embodiment, the circuitous path may be a continuous loop.

The track of the active floor assembly may include a plurality of corners 230 around which the floor must bend around in order to follow the track. One or more of the corners may change the direction of the floor at different angles. A roller assembly 260, including a roller or bearing may be provided at one or more corners in order to facilitate the floor following the track around corners.

In an example embodiment, the floor may be comprised of at least two sections which may be moved independently of each other. Independent movement facilitates the width W of the opening to be variable in to accommodate different portions of the proton beam generator and/or nozzle to protrude through the active floor as necessary while minimizing the amount of open floor exposed.

In an embodiment, one or more motors or drive mechanisms 270 may be provided to drive the floor along the track. Two drives facilitate independent movement the two moving floor sections.

In an embodiment, FIG. 4a illustrates an active floor configured for situations wherein the proton beam nozzle is completely disposed vertically above the active floor, such as is illustrated in FIGS. 2a-c.

Figure 4B:
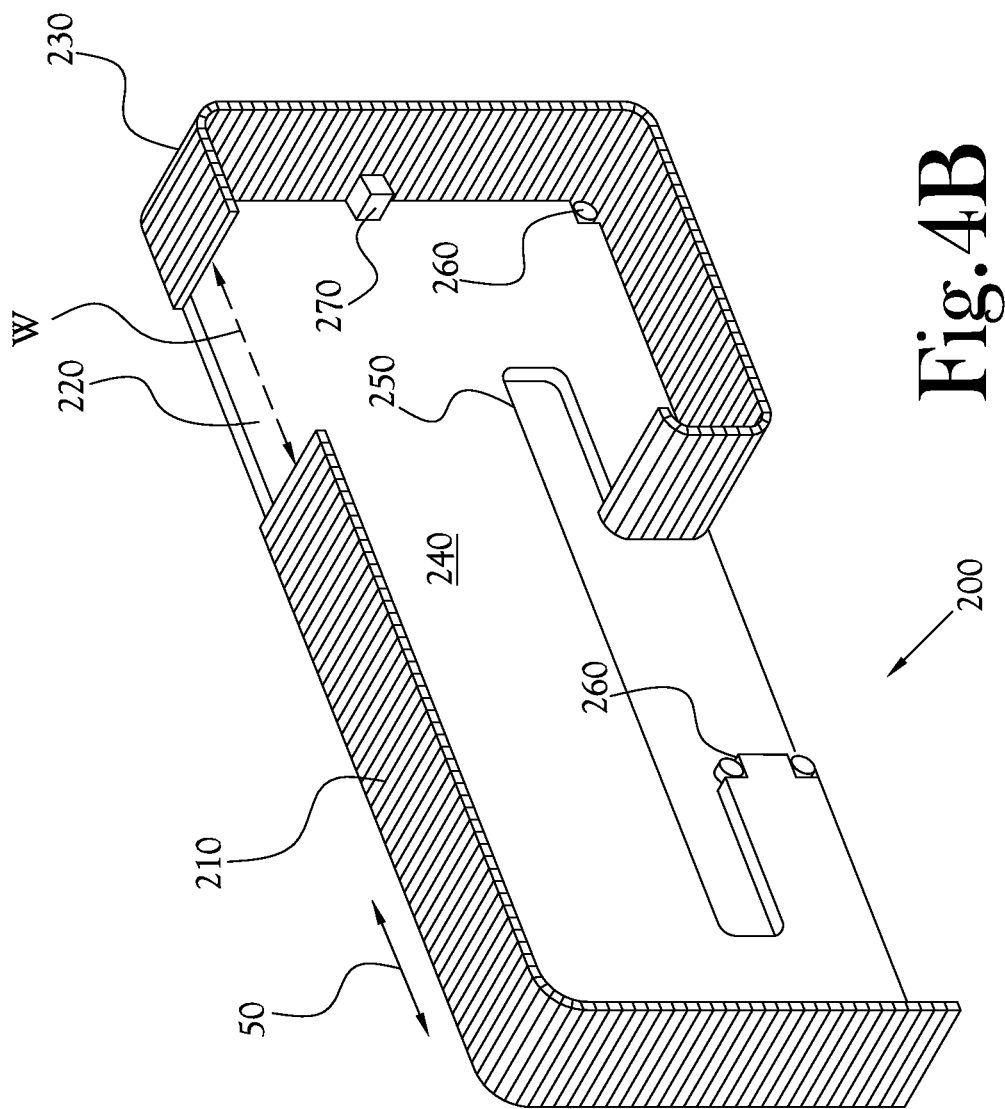

In an embodiment, FIG. 4b illustrates an active floor configured for situations wherein the proton beam nozzle is partially disposed vertically below the active floor and protruding through an opening 220 in the active floor, such as is illustrated in FIG. 2d.

Figure 4C:
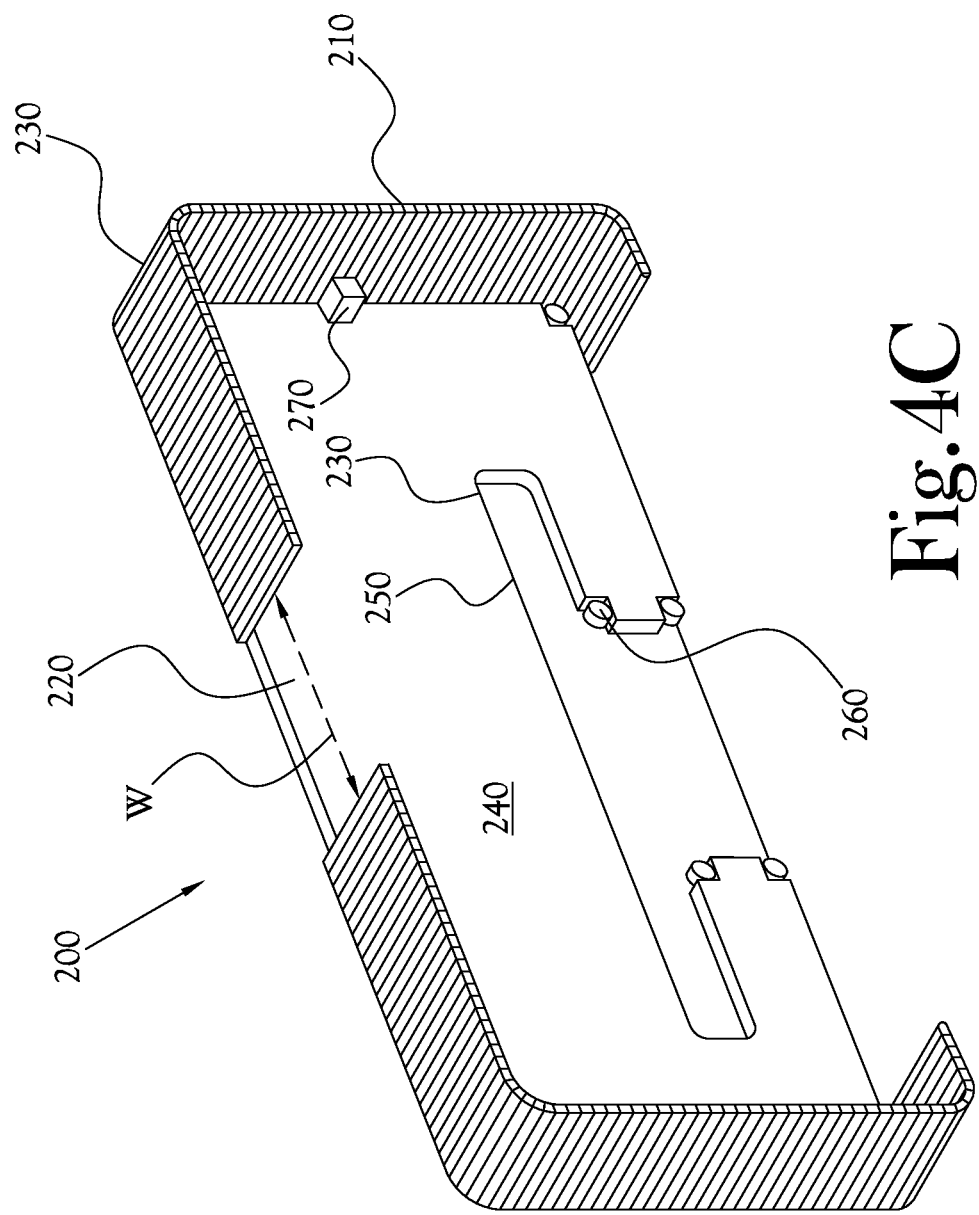

In an embodiment, FIG. 4c illustrates an active floor configured for situations wherein the proton beam nozzle is partially disposed vertically below the active floor and protruding through an opening 220 in the active floor, such as is illustrated in FIG. 2e.

In an embodiment, FIG. 4d illustrates an active floor configured for situations wherein the proton beam nozzle is partially disposed vertically below the active floor and protruding through an opening 220 in the active floor, such as is illustrated in FIG. 2f.

It is to be noted that the angular position of the proton beam nozzle in FIGS. 2a-2f may be referred to be as approximately 0°, 45°, 0°, 90°, 225°, 270°, and 315°, respectively.

FIG. 5 illustrates an example embodiment of a slat 218 utilized with a plurality of other slats to make up an active floor. The slat may be comprised of a beam 290 constructed of a material strong enough to hold the weight of one or more operators and perhaps equipment for operating or servicing the proton beam system. A top layer 292 of surface material may be provided on top of the beam 290. The top layer may be comprised of a non-slip material that provides cushioning and/or sound dampening. The slat 218 may have a tongue 294 provided on an end for fitting within a track in order for the slats to follow the path of the track. One or more brackets 296 may be disposed on the bottom of the beam. The brackets may be configured to have holes 298 which receive pins 300. Brackets on adjacent beams may be rotatably interconnected by aligning holes on the brackets of adjacent or contiguous slats and inserting the pins through the bracket holes of the slats.

Figure 6A:
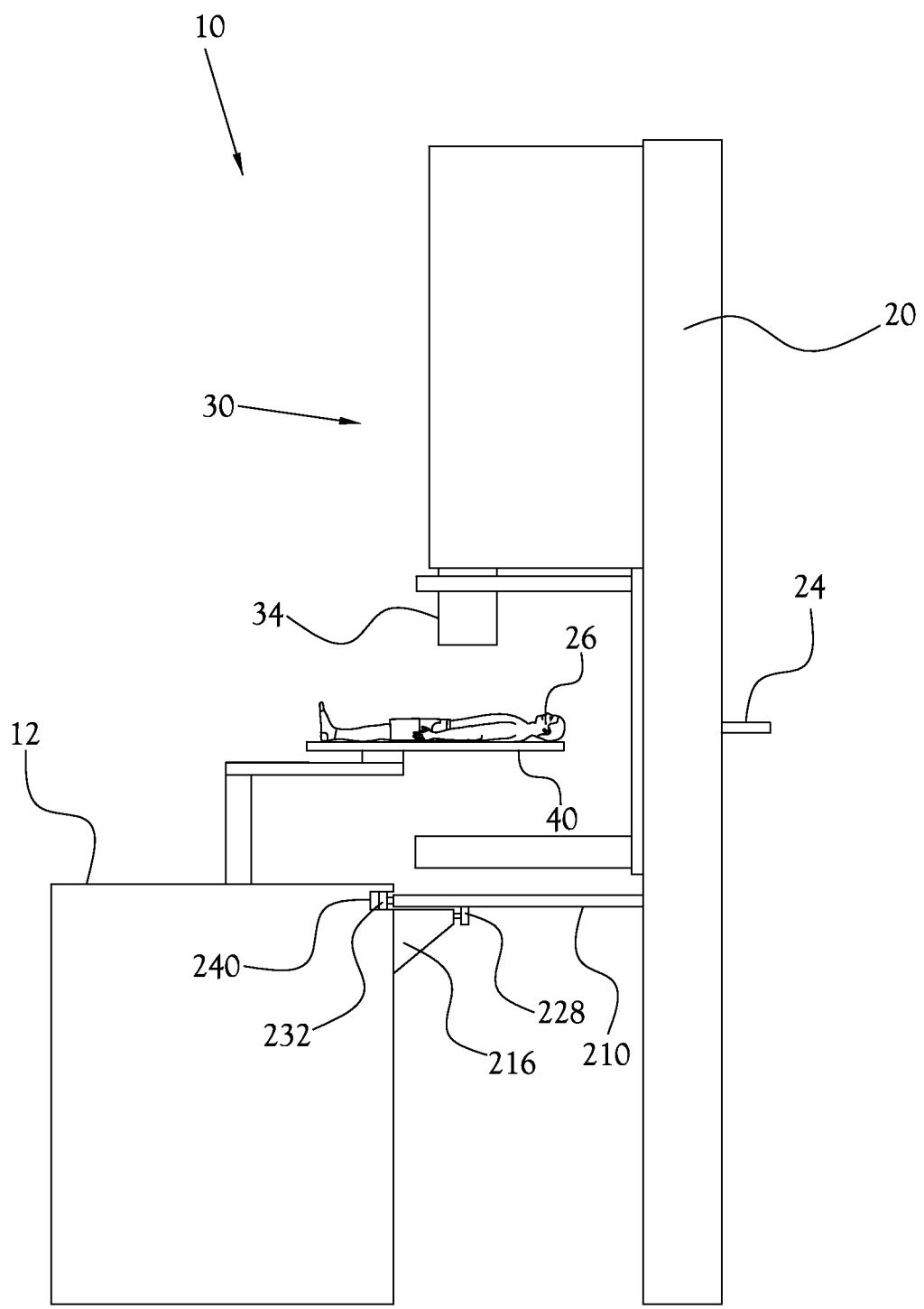
FIG. 6A is a graphic schematic side view diagram of an example embodiment of a proton therapy system.
Figure 6B:
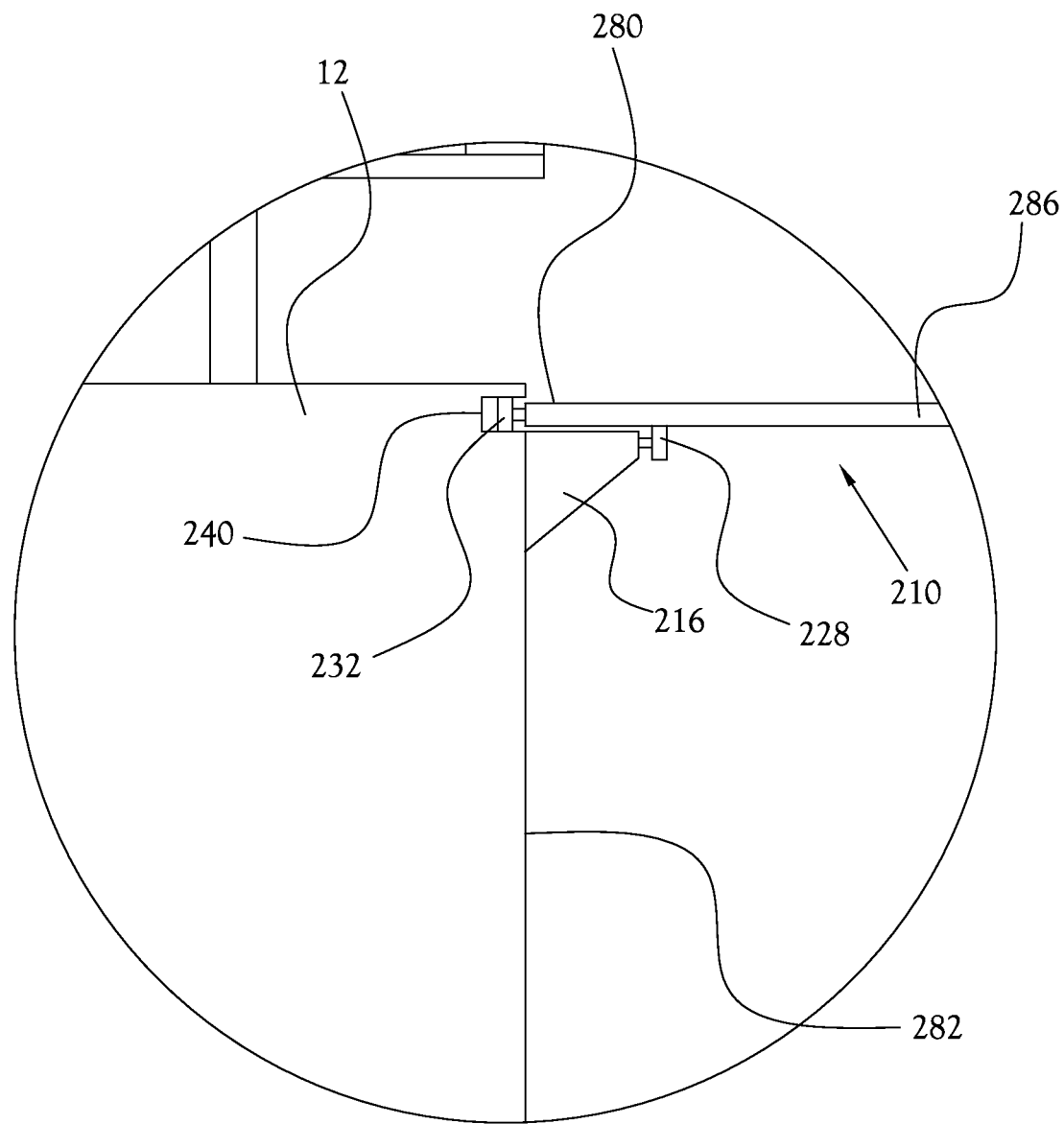
FIG. 6B is a graphic schematic side view diagram of an example embodiment of a proton therapy system.

FIGS. 6 and 6B illustrate an example embodiment of a proton therapy (PT) system 10 wherein a gantry wheel 20 rotates a proton beam generator 30 about an axis of rotation 24. The proton beam generator directs a proton beam through a nozzle 34 from any angle between zero and 380 degrees toward a patient 26 lying on bed 40 near the isocenter of the gantry wheel. The gantry system 10 may include a mezzanine platform 12 and active (or rolling) floor 210 for a technician to walk on, enabling a technician to access magnets, nozzles, achromat and hoses from a beamline and cooling system, etc. for service or replacement. The active floor may be supported by a rail frame 216 attached to a stationary support system or mezzanine 12.

The active floor 210 may roll on a roller 228 attached to the rail frame 216 and a roller 232 disposed in a track 240 provided in the stationary support 44.

It is important for the therapist to be able to assume a position proximate the rotating wheel during the treatment setup. The rolling floor serves to accomplish this end. In order the support a therapist or other person on the rolling floor proximate the rotating wheel 20, it is desirable for the rolling floor 210 to be cantilevered as is shown in FIGS. 6 and 6B. This cantilevered rolling floor 210 includes one side portion 280 that is provided with a roller 232 received within a track 240 in the floor 12 of the gantry room. A further roller 228 extends outwardly from the wall 282 as shown in FIG. 6B. This roller 228 supports the floor 210 at a location spaced from the side portion 280 carrying the roller 232. In this manner, the opposite side portion 944 of the floor 904 can be cantilevered while still providing sufficient support for the weight of the therapist or other person needing to stand proximate the rotating wheel 902.

Figure 7:
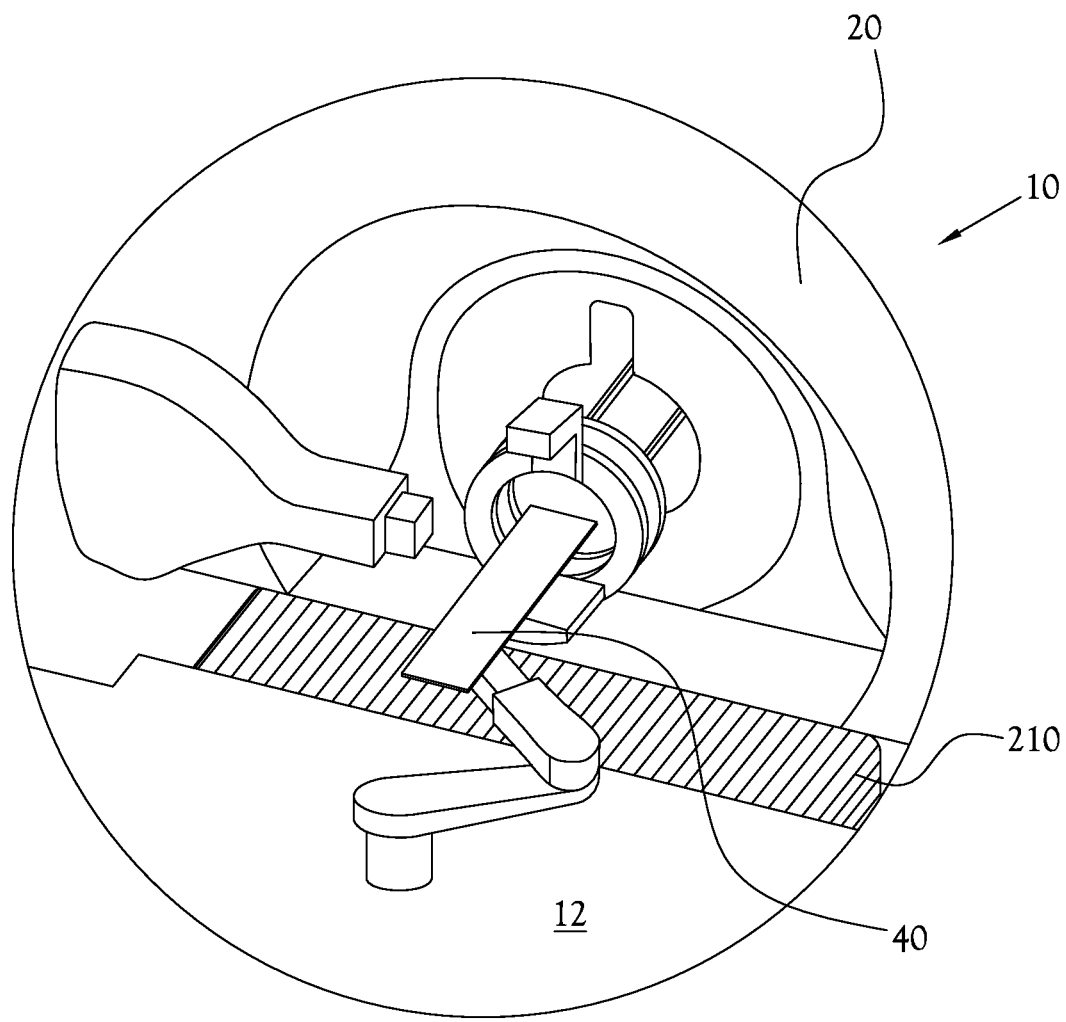
FIG. 7 is an isometric cutaway view of an example embodiment proton therapy system.

FIG. 7 illustrates an example embodiment of a proton therapy (PT) system 10 wherein a gantry wheel 20 rotates a proton beam generator about an axis of rotation 24. The proton beam generator directs a proton beam through a nozzle toward a patient lying on bed 40 positioned near the isocenter of the gantry wheel. The gantry system may include a mezzanine platform 12 and active (or rolling) floor 210 for a technician to walk on, enabling a technician to access magnets, nozzles, achromat and hoses from a beamline and cooling system, etc. for service or replacement. The active floor may be supported by a rail frame 216 attached to a stationary support system or mezzanine 12. The active floor 210 may roll on a roller 228 attached to the rail frame 216 and a roller 232 disposed in a track 240 provided in the stationary support 44.

Figure 8:
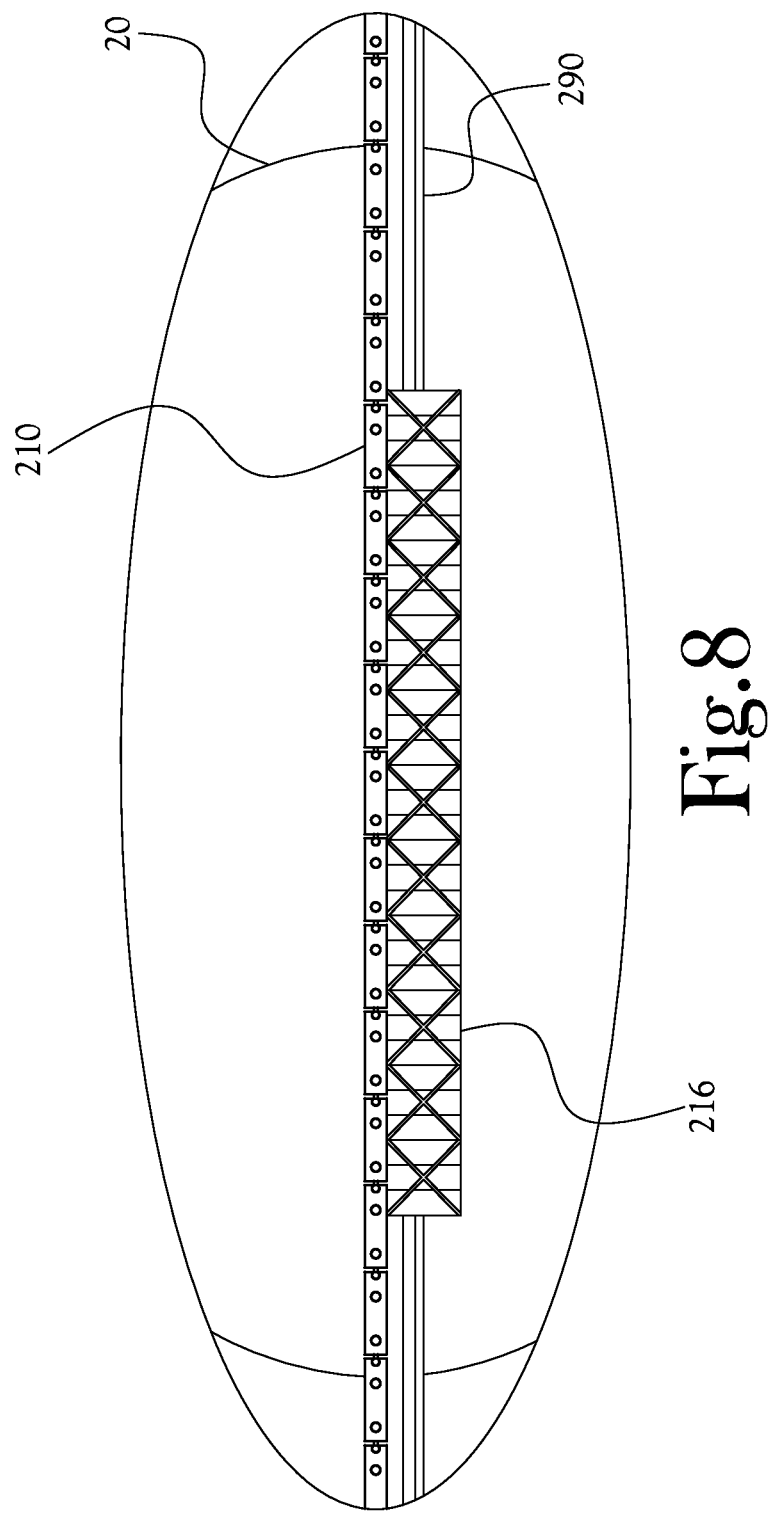
FIG. 8 is a cutaway front view of an example embodiment proton therapy system.

FIG. 8 illustrates an example embodiment of a proton therapy (PT) system 10 wherein a gantry wheel 20 rotates a proton beam generator about an axis of rotation 24. The proton beam generator directs a proton beam through a nozzle toward a patient positioned near the isocenter of the gantry wheel. The gantry system may include an active (or rolling) floor 210 for a technician to walk on, enabling a technician to access magnets, nozzles, achromat and hoses from a beamline and cooling system, etc. for service or replacement. The active, or moving, floor may be supported by a rail frame 216 attached to a stationary support system 290.

Figures 9, 10:
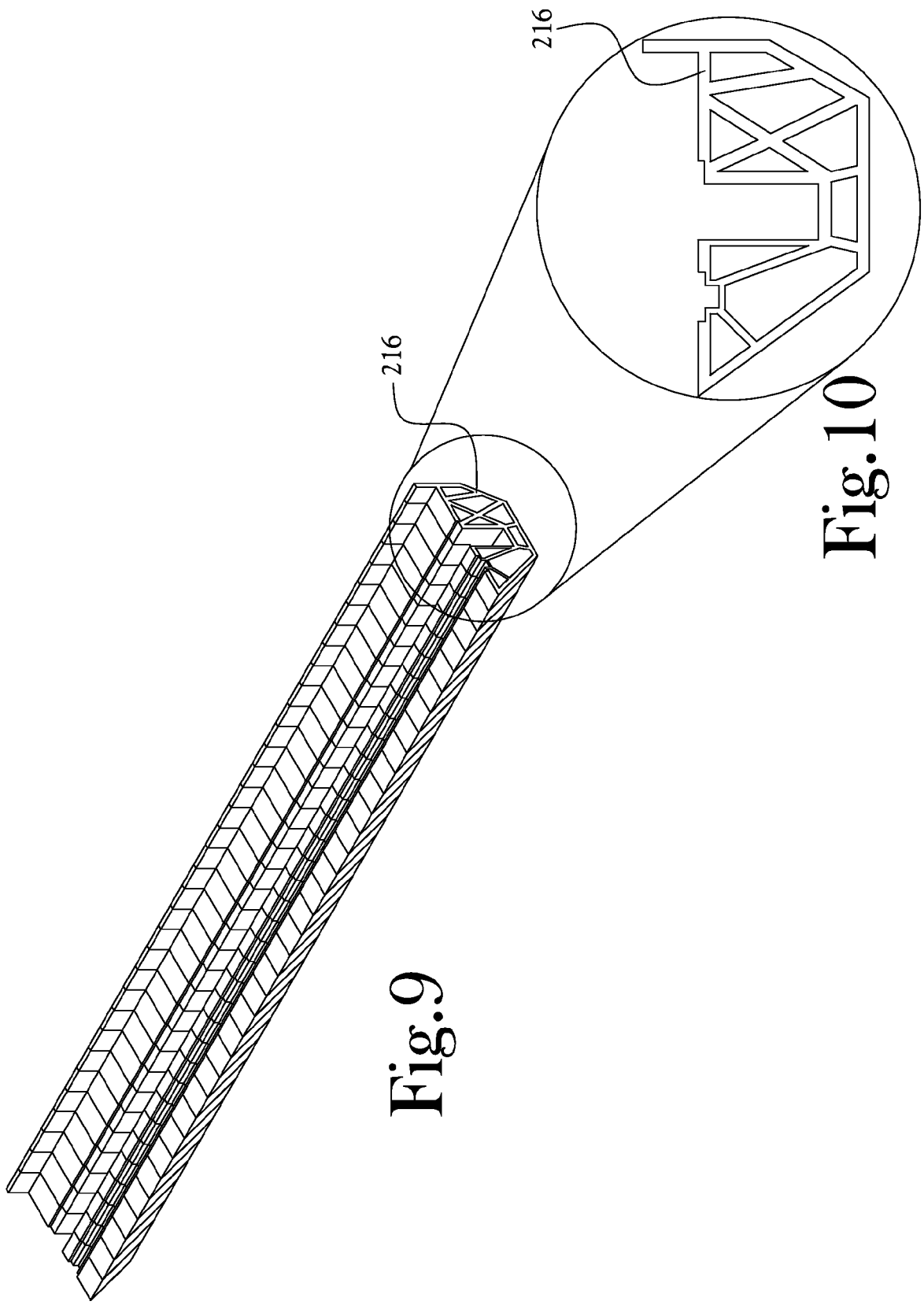
FIG. 9 is an isometric diagram of an example embodiment rail for an active floor system.
FIG. 10 is an end view diagram of an example embodiment rail for an active floor system.

FIGS. 9 and 10 illustrate an example embodiment of a rail frame 216 that may be utilized to support an active floor system. The frame may be constructed in the form of a lattice.

Figure 11:
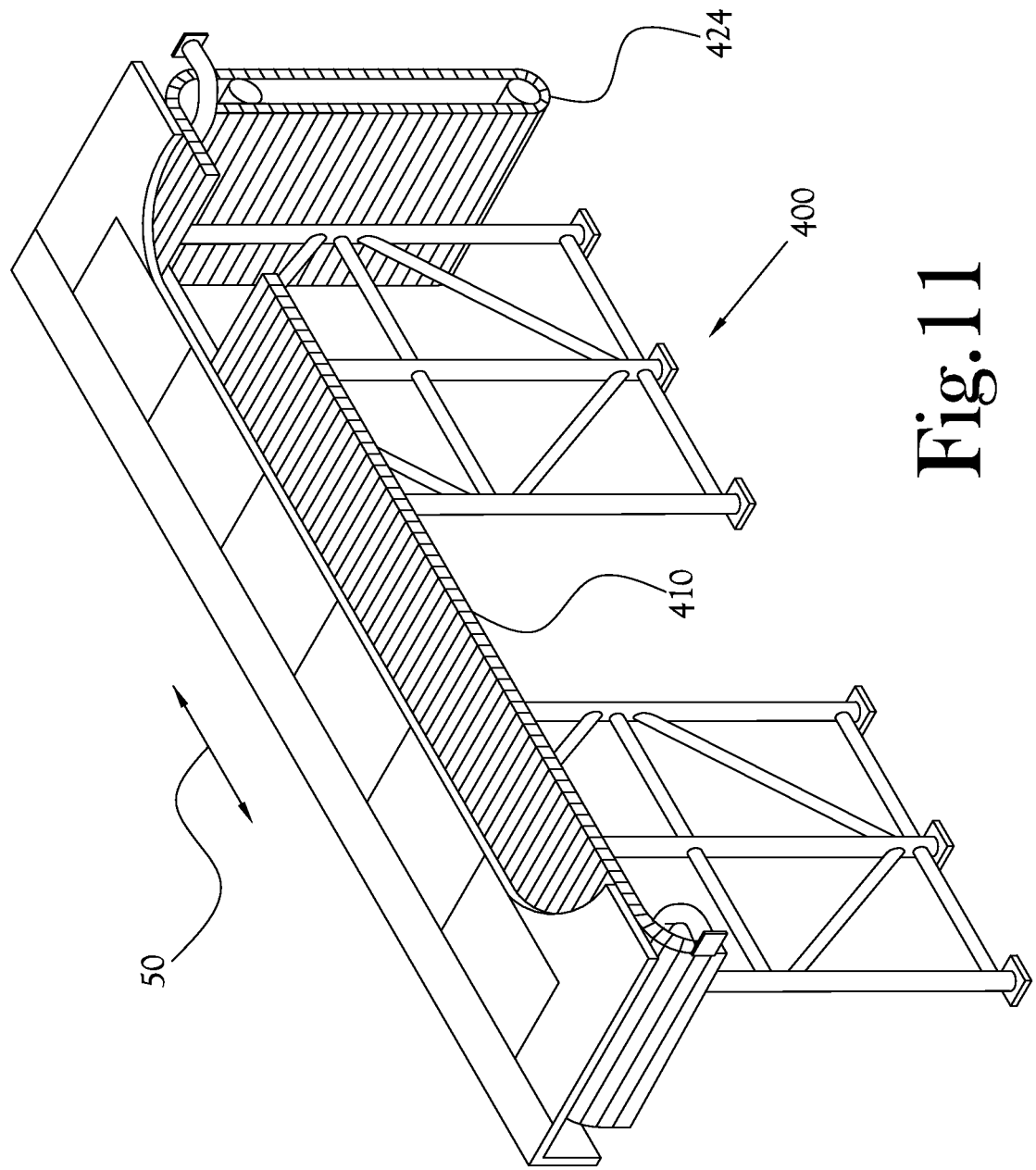
FIG. 11 is isometric view of an example embodiment of a partially built active floor system.

FIG. 11 illustrates an example embodiment of an active floor system 400, wherein a floor 410 moves in a lateral back and forth direction illustrated by arrow 50. The floor may be comprised of a plurality of rotatable interconnected slats. The floor may move or slide in a path that includes a hanging loop. The track(s) 250 keeps the active moving floor captured in place and provides support so that the track does not bow or become displaced from the weight of an operator standing of the floor.

In an example embodiment, the end portions of the moving floor are terminated at points which are located within a housing. The housing has a circuitous track provided therein wherein the floor follows a circuitous route because it is captured within the circuitous track. These ends reduce the motor load by a factor of two because half the weight is supported on the terminated end. Opposite end portions terminate in ends which cooperate with each other to selectively define an opening having a dimension which is controlled for receiving a proton beam nozzle therein as the nozzle rotates below a patient positioned on a bed. Thus, the nozzle mounted on the rotating gantry or wheel passes below the floor and moves to a selected location below the patient as is shown. During rotation of the nozzle on the rotating wheel, it will be noted that the opening defined by the opposite ends of the first and second moving sections changes in location and size to accommodate the nozzle travel yet minimizes the opening size such that an operator or therapist may stand on the active floor without falling through the opening when the floor is stationary.

An example embodiment operator support apparatus for a proton treatment system, comprises: a proton beam nozzle to emit a proton beam to a targeted region of a patient; gantry wheel having a front face to support the proton beam nozzle to direct the proton beam approximately to an isocenter of the gantry wheel corresponding to the targeted region, wherein the gantry wheel rotates the proton beam nozzle around the isocenter; an active floor that horizontally translates across the front face of the gantry wheel, the active floor having an opening having a width through which the proton beam nozzle protrudes when the proton beam nozzle is located below the targeted region.

In an example embodiment, the active floor is comprised of a plurality of interconnected slats wherein adjacent slats pivot with respect to each other. In an example embodiment, the active floor is comprised of a first section and a second section, wherein the first and second sections move independently of each other. In an example embodiment, the active floor is comprised of a first section and a second section, wherein the first and second sections move independently of each other and the opening width is variable. In an example embodiment, the active floor is comprised of a plurality of interconnected slats arranged in at least two sections, wherein adjacent slats pivot with respect to each other and a first section translates through a channel around a first corner from horizontal movement to non-horizontal movement and a second section translates through a channel around a second corner from horizontal movement to non-horizontal movement.

It is important for a therapist to be able to assume a position proximate the rotating wheel during proton treatment setup. The active floor serves to accomplish this.

In an example embodiment, the slats of the active floor may be cantilevered wherein one side portion is provided with a roller received within a track in the floor system of the gantry room. A further roller extends outwardly from a wall and supports the floor at a location spaced from the side portion carrying the roller. In this manner, the opposite side portion of the floor may be cantilevered while still providing sufficient support for the weight of the therapist or other person needing to stand proximate the rotating wheel.

Figure 12:
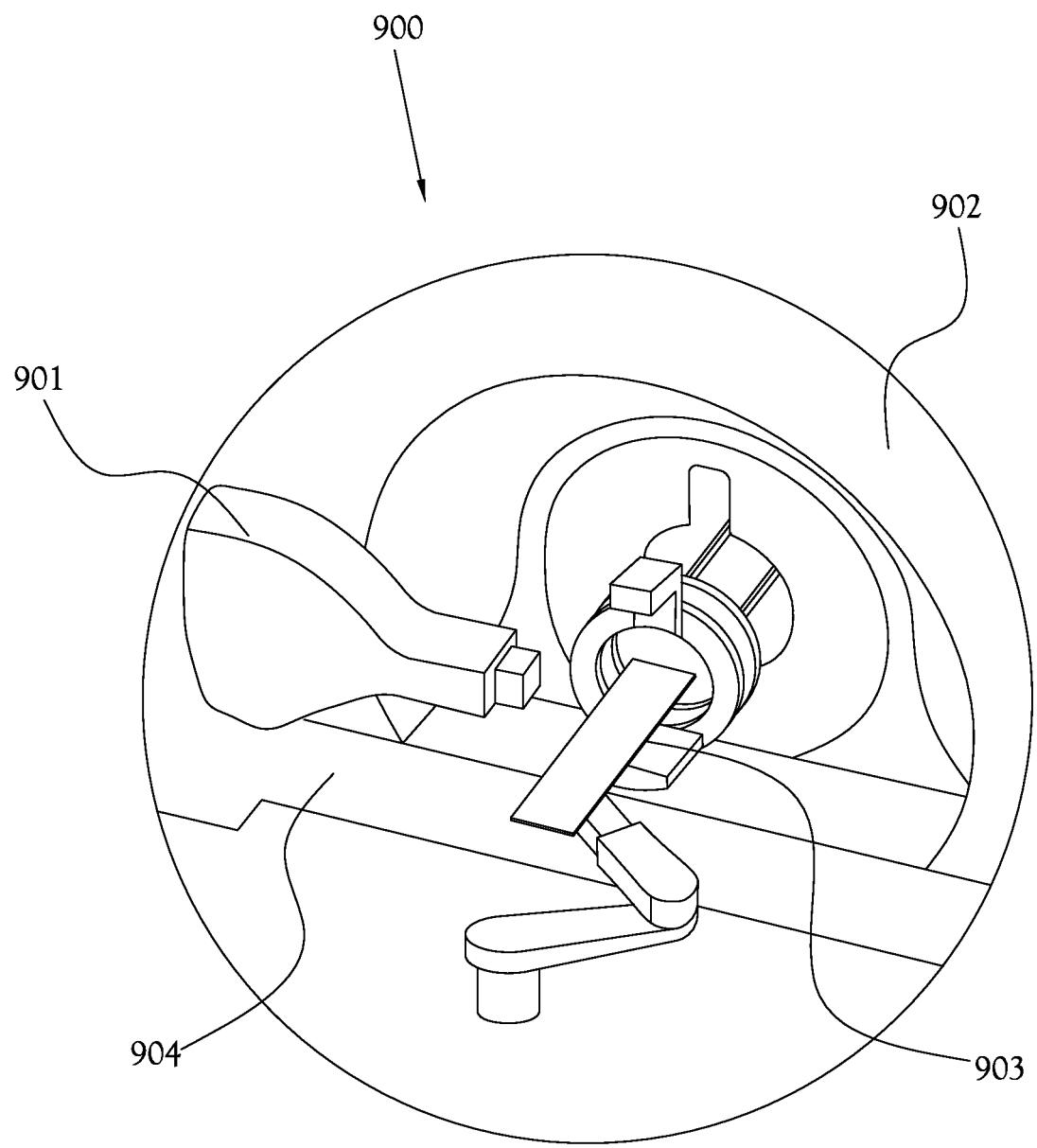
FIG. 12 a graphic illustration of a proton therapy system and environment configured in accordance with an example embodiment of the present general inventive concept.

FIG. 12 is a graphic illustration of a proton therapy system 900 and environment configured in accordance with an example embodiment of the present general inventive concept.

FIGS. 12, 13A to 13D illustrate various views depicting a rolling floor arrangement to provide clearance for the rotating gantry and beam nozzle apparatus, for example when the beam nozzle is rotated underneath the patient, according to example embodiments of the present general inventive concept.

Figure 13A:
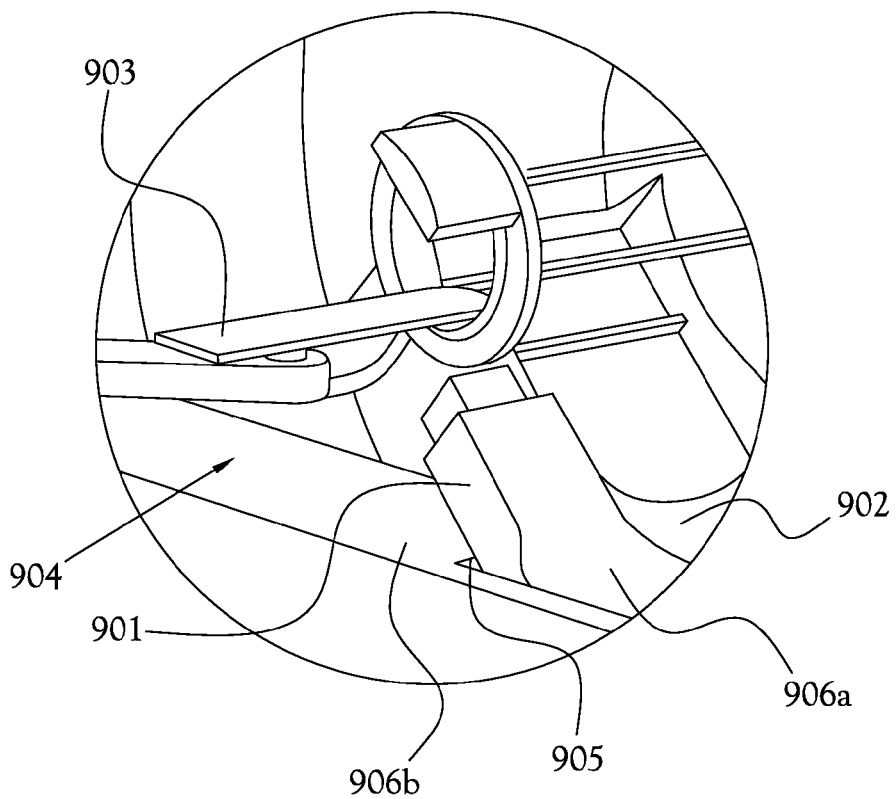
FIGS. 13A to 13D illustrate various view depicting a rolling floor arrangement to provide clearance for the rotating gantry and beam nozzle apparatus, for example when the beam nozzle is rotated underneath the patient, according to example embodiments of the present general inventive concept.

As shown in FIGS. 12 and 13A, the nozzle 901 is mounted on the rotating wheel 902 of the proton treatment gantry. In order to enable the nozzle 901 to rotate above and below a patient positioned on a support bed 903, a rolling floor 904 is provided. This rolling floor selectively defines an opening 905 into, and out of, which the nozzle 901 moves during rotation of the rotating wheel 902.

Figure 13B:
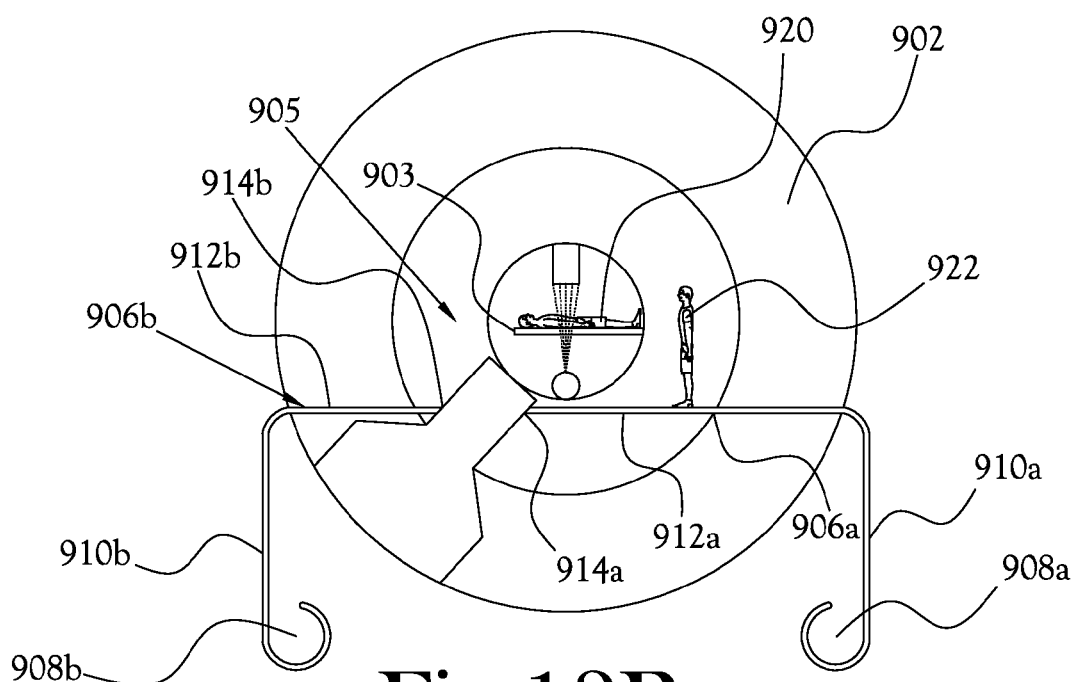
Figure 13C:
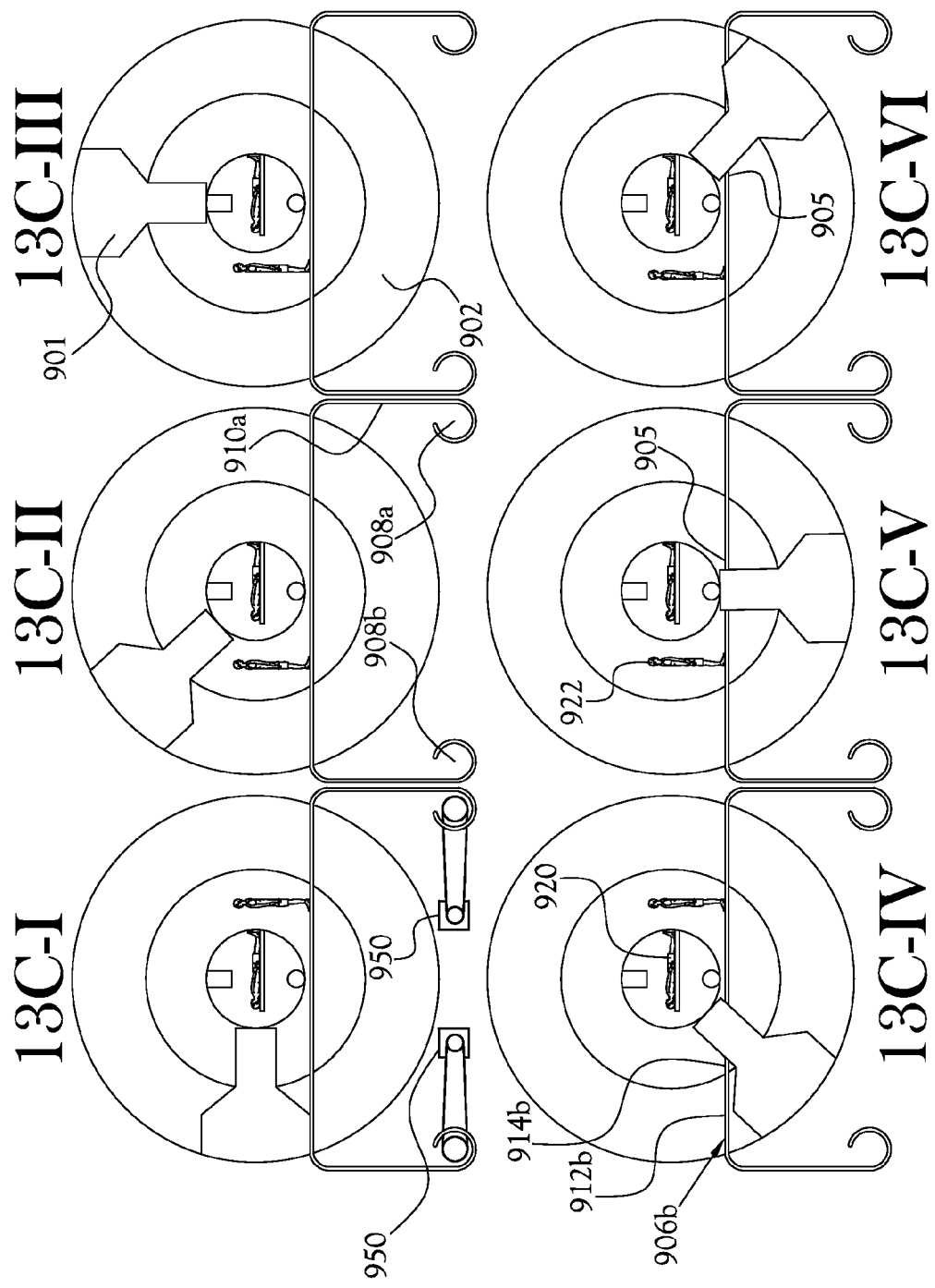
Figure 13D:
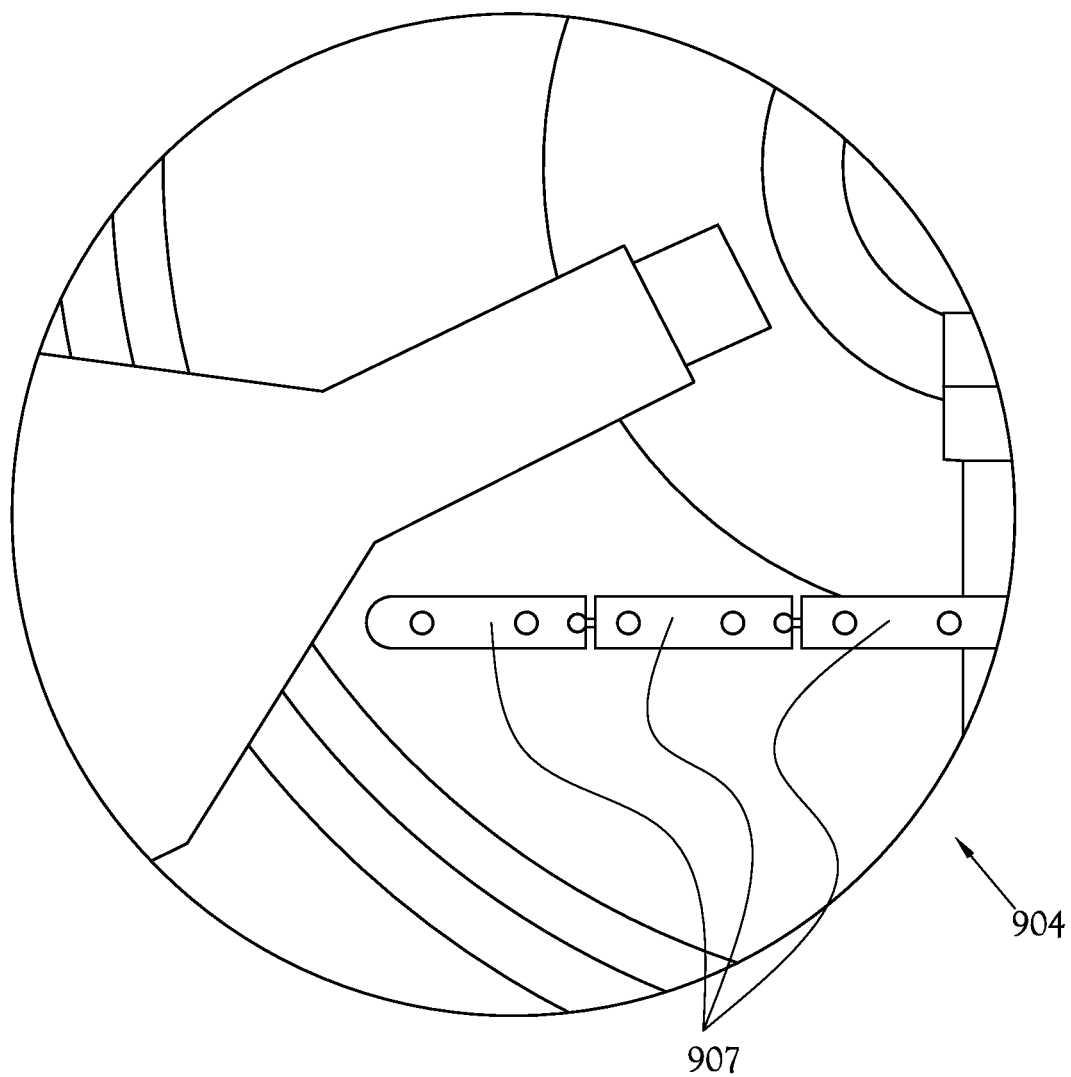

More specifically, the rolling floor 904 includes a first section 906a fabricated, in one embodiment, from a plurality of interconnected slats as shown at 907 in FIG. 13D. These interconnected slats can be rotatably mounted on a take-up roll 908a and 908b.

Similarly, a second section 906b of the rolling floor 904 (See FIG. 13B) is likewise provided with a plurality of interconnected slats similar to the slats shown at 907 in FIG. 13D. The end portion 910a of the floor section 906a is mounted on a take-up roll 908a illustrated diagrammatically in FIG. 13B. The opposite end portion 912b terminates in an end 914b which cooperates with the end 914a of the first section of the rolling floor to selectively define an opening 905 having a dimension which is controlled for receiving the nozzle therein as the nozzle rotates below a patient 920 positioned on the bed 903.

As shown in FIG. 13C(I-VI) the nozzle is received in the opening 905 as the nozzle rotates about a patient. Thus, the nozzle mounted on the rotating wheel passes below the rolling floor and moves to a selected location below the patient as is shown in FIG. 13B. During this rotation of the nozzle on the rotating wheel 902, it will be noted that the opening 905 defined by the opposite ends of the first and second rolling sections changes in location and size to accommodate the nozzle travel yet minimizes the opening size such that a therapist 922 can stand on the rolling floor without falling through the opening 905 when the rolling floor is stationary.

A drive mechanism shown diagrammatically at 950 in FIG. 13C-I serves to rotate the take-up rolls 908a and 908b to move the opening 905 along the rolling floor to accommodate the nozzle rotation above and below the patient. The speed and direction of the rotation of the drive mechanism controls the size and locate of the opening 905 as it moves along the rolling floor 904. The movement of the nozzle 901 and corresponding movement of the opening 905 in the rolling floor is shown in FIGS. 13C-IV, 13C-V and 13C-VI. FIGS. 13C-I, 13C-II and 13C-III illustrate movement of the nozzle as it rotates on the rotating wheel 902 above the rotating floor.

In an example embodiment, a rolling floor for supporting a person proximate the nozzle mounted on the rotating wheel of a proton treatment gantry, the rolling floor includes: a first section having one end portion rotatably mounted on a take-up roll and defining an opposite end portion terminating in an opening end of the first section; a second section having one end portion rotatably mounted on a take-up roll and defining an opposite end portion terminating in an opening end which cooperates with the opening end; a drive mechanism for selectively discharging and taking up, said first and said second sections of said rolling floor onto and from the respective take-up rolls; and an opening selectively defined between the opening ends of said first and said second section, said opening size being selected for receiving said nozzle therethrough as said nozzle mounted on said rotating wheel passes below and above said rolling floor during rotation of said nozzle about a patient during proton treatment. The first and second sections of the rolling floor may include a plurality of interconnected slats wherein adjacent slats pivot with respect to each other.

It is noted that the simplified diagrams and drawings do not illustrate all the various connections and assemblies of the various components, however, those skilled in the art will understand how to implement such connections and assemblies, based on the illustrated components, figures, and descriptions provided herein, using sound engineering judgment.

Numerous variations, modifications, and additional embodiments are possible, and accordingly, all such variations, modifications, and embodiments are to be regarded as being within the spirit and scope of the present general inventive concept. For example, regardless of the content of any portion of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity may be repeated, any activity may be performed by multiple entities, and/or any element may be duplicated.

While the present general inventive concept has been illustrated by description of several example embodiments, it is not the intention of the applicant to restrict or in any way limit the scope of the inventive concept to such descriptions and illustrations. Instead, the descriptions, drawings, and claims herein are to be regarded as illustrative in nature, and not as restrictive, and additional embodiments will readily appear to those skilled in the art upon reading the above description and drawings.

The invention claimed is:

1. An operator support apparatus for a proton treatment system, comprising:
   a proton beam nozzle to emit a proton beam to a targeted region of a patient;
   a gantry wheel having a front face to support the proton beam nozzle to direct the proton beam approximately to an isocenter of the gantry wheel corresponding to the targeted region, wherein the gantry wheel rotates the proton beam nozzle around the isocenter about a rotation axis of the gantry wheel; and
   a moving floor having an upper surface to support an operator of the proton treatment system, the moving floor being configured to move across the front face laterally relative to the rotation axis, the moving floor including an opening having a width through which the proton beam nozzle protrudes when at least a portion of the proton beam nozzle is located below the upper surface of the moving floor.

2. The operator support apparatus of claim 1 wherein the moving floor is comprised of a plurality of interconnected slats wherein adjacent slats pivot with respect to each other.

3. The operator support apparatus of claim 1 wherein the moving floor is comprised of a first section and a second section, wherein the first and second sections move independently of each other.

4. The operator support apparatus of claim 1 wherein the moving floor is comprised of a first section and a second section, wherein the first and second sections move independently of each other and the opening width is variable.

5. The operator support apparatus of claim 1 wherein the moving floor is comprised of a plurality of interconnected slats arranged in at least two sections, wherein adjacent slats pivot with respect to each other and a first section translates through a channel around a first corner from horizontal movement to non-horizontal movement and a second section translates through a channel around a second corner from horizontal movement to non-horizontal movement.

6. The operator support apparatus of claim 1 wherein the moving floor is comprised of a circuitous path in a continuous loop.

7. The operator support apparatus of claim 1 comprising a track through which the moving floor moves, the track having a plurality of corners around which the floor must bend around in order to follow the track.

8. A rolling floor for supporting a person proximate the nozzle mounted on the rotating wheel of a proton treatment gantry, the rolling floor including:
   a first section having one end portion rotatably mounted on a take-up roll and defining an opposite end portion terminating in an opening end of the first section;
   a second section having one end portion rotatably mounted on a take-up roll and defining an opposite end portion terminating in an opening end which cooperates with the opening end;
   a drive mechanism for selectively discharging and taking up, said first and said second sections of said rolling floor onto and from the respective take-up rolls; and
   an opening selectively defined between the opening ends of said first and said second section, said opening size being selected for receiving said nozzle therethrough as said nozzle mounted on said rotating wheel passes below and above said rolling floor during rotation of said nozzle about a patient during proton treatment.

9. The rolling floor of claim 8 wherein said first and second sections of said rolling floor each include a plurality of interconnected slats wherein adjacent slats pivot with respect to each other.

10. A method of operating a proton treatment system, comprising:
   emitting a proton beam to a targeted region of a patient utilizing a proton beam nozzle;
   rotating the proton beam nozzle around the targeted region utilizing a gantry wheel having a rotation axis and a front face to support the proton beam nozzle to direct the proton beam approximately to an isocenter of the gantry wheel corresponding to the targeted region; and
   translating a floor across the front face of the gantry wheel laterally relative to the rotation axis, the floor having an upper surface to support an operator of the proton treatment system and an opening having a width through which the proton beam nozzle protrudes when at least a portion of the proton beam nozzle is located below the upper surface.

11. The method of claim 10 wherein the floor is comprised of a plurality of interconnected slats wherein adjacent slats pivot with respect to each other.

12. The method of claim 10 wherein the floor is comprised of a first section and a second section, wherein the first and second sections move independently of each other.

13. The method of claim 10 wherein the floor is comprised of a first section and a second section, wherein the first and second sections move independently of each other and the opening width is variable.

14. The method of claim 10 wherein the floor is comprised of a plurality of interconnected slats arranged in at least two sections, wherein adjacent slats pivot with respect to each other and a first section translates through a channel around a first corner from horizontal movement to non-horizontal movement and a second section translates through a channel around a second corner from horizontal movement to non-horizontal movement.

15. The method of claim 10 wherein the floor is comprised of a circuitous path in a continuous loop.

16. The method of claim 10 comprising a track through which the floor moves, the track having a plurality of corners around which the floor must bend around in order to follow the track.

17. A method of operating a proton treatment system, comprising:
    emitting a proton beam to a targeted region of a patient utilizing a proton beam nozzle;
    rotating the proton beam nozzle around the targeted region utilizing a rotating wheel having a front face to support the proton beam nozzle to direct the proton beam approximately to an isocenter of the rotating wheel corresponding to the targeted region;
    translating a rolling floor across the front face of the rotating wheel for supporting a person proximate the nozzle mounted on the rotating wheel of a proton treatment gantry, the rolling floor including:
        a first section having one end portion rotatably mounted on a take-up roll and defining an opposite end portion terminating in an opening end of the first section;
        a second section having one end portion rotatably mounted on a take-up roll and defining an opposite end portion terminating in an opening end which cooperates with the opening end;
        a drive mechanism for selectively discharging and taking up, said first and said second sections of said rolling floor onto and from the respective take-up rolls; and
        an opening selectively defined between the opening ends of said first and said second section, said opening size being selected for receiving said nozzle therethrough as said nozzle mounted on said rotating wheel passes below and above said rolling floor during rotation of said nozzle about a patient during proton treatment.

18. The method of claim 17 wherein said first and second sections of said rolling floor each include a plurality of interconnected slats wherein adjacent slats pivot with respect to each other.

19. A moving floor for use in a proton treatment system, the proton treatment system including a proton beam nozzle to emit a proton beam to a targeted region of a patient and a gantry wheel having a front face to support the proton beam nozzle such that the proton beam nozzle directs the proton beam toward an isocenter of the gantry wheel corresponding to the targeted region, the gantry wheel being configured to rotate the proton beam nozzle around the isocenter about a rotation axis of the gantry wheel, the moving floor comprising:
    a plurality of interconnected slats having an upper surface to support an operator of the proton treatment system, the plurality of interconnected slats defining an opening through which an end of the proton beam nozzle protrudes when at least a portion of the proton beam nozzle is located below the upper surface; and
    a drive mechanism to move the plurality of interconnected slats across the front face of the gantry wheel laterally relative to the rotation axis such that the end of the proton beam nozzle protrudes through the opening when the at least a portion of the proton beam nozzle is rotated below the upper surface.

20. The moving floor of claim 19, wherein the plurality of interconnected slats comprises a first section of interconnected slats and a second section of interconnected slats located at opposing sides of the opening, respectively, the first and second sections being configured to move independently of each other to vary a width of the opening such that the opening accommodates different portions of the proton beam nozzle depending upon which portion of the at least a portion of the proton beam nozzle is located below the upper surface.

* * * * *